(12) United States Patent
Larsen

(10) Patent No.: US 8,608,079 B2
(45) Date of Patent: Dec. 17, 2013

(54) CONTACT FREE READING OF CARTRIDGE IDENTIFICATION CODES

(75) Inventor: André Larsen, Dragør (DK)

(73) Assignee: Novo Nordisk A/S, Bagsvaerd (DK)

( * ) Notice: Subject to any disclaimer, the term of this patent is extended or adjusted under 35 U.S.C. 154(b) by 731 days.

(21) Appl. No.: 12/293,251

(22) PCT Filed: Mar. 20, 2007

(86) PCT No.: PCT/EP2007/052634
§ 371 (c)(1),
(2), (4) Date: Oct. 13, 2008

(87) PCT Pub. No.: WO2007/107562
PCT Pub. Date: Sep. 27, 2007

(65) Prior Publication Data
US 2009/0088701 A1 Apr. 2, 2009

Related U.S. Application Data

(60) Provisional application No. 60/788,204, filed on Mar. 31, 2006.

(30) Foreign Application Priority Data

Mar. 20, 2006 (EP) ..................................... 06005597

(51) Int. Cl.
*G06K 19/06* (2006.01)
(52) U.S. Cl.
USPC ...................................... 235/492; 340/572.1
(58) Field of Classification Search
USPC ................................................ 235/387, 492
See application file for complete search history.

(56) References Cited

U.S. PATENT DOCUMENTS

| 3,700,862 A | 10/1972 | Snook et al. |
| 3,809,863 A | 5/1974 | Oberg |
| 3,916,157 A | 10/1975 | Roulette et al. |
| 3,998,513 A | 12/1976 | Kobayashi et al. |
| 4,179,212 A | 12/1979 | Lahr |
| 4,327,283 A | 4/1982 | Henman et al. |

(Continued)

FOREIGN PATENT DOCUMENTS

| CN | 1013704 | 8/1991 |
| CN | 1051152 | 9/1993 |

(Continued)

OTHER PUBLICATIONS

English Abstract for DE4402319.

(Continued)

*Primary Examiner* — Christopher Stanford
(74) *Attorney, Agent, or Firm* — Wesley A. Nicolas; Marc A. Began; Reza Green

(57) ABSTRACT

The present invention relates to a cartridge adapted to contain a medicament, the cartridge further being adapted to be inserted into an associated medication delivery device. The cartridge according to the present invention comprises a plurality of electrode elements arranged on an exterior surface part of the cartridge, wherein an electrode element of said plurality of electrode elements comprises a receiver zone and a transmitter zone, said receiver and transmitter zones being electrically connected. The receiver and transmitter zones are adapted to electrically couple to one or more transmitters and to one or more receivers, respectively, said one or more transmitters and said one or more receivers being arranged on the associated medication delivery device.

15 Claims, 10 Drawing Sheets

(56) References Cited

U.S. PATENT DOCUMENTS

| | | |
|---|---|---|
| 4,355,300 A | 10/1982 | Weber |
| 4,420,754 A | 12/1983 | Andermo |
| 4,449,042 A | 5/1984 | Hampson et al. |
| 4,476,149 A | 10/1984 | Poppe et al. |
| 4,476,381 A | 10/1984 | Rubin |
| 4,591,707 A | 5/1986 | Stenzel et al. |
| 4,625,101 A | 11/1986 | Hinks et al. |
| 4,636,786 A | 1/1987 | Haertling |
| 4,693,574 A | 9/1987 | Ohnuki et al. |
| 4,731,526 A | 3/1988 | Knoll et al. |
| 4,739,377 A | 4/1988 | Allen |
| 4,810,867 A | 3/1989 | Speicher |
| 4,850,966 A | 7/1989 | Grau et al. |
| 4,853,521 A | 8/1989 | Claeys et al. |
| 4,857,716 A | 8/1989 | Gombrich et al. |
| 4,880,014 A | 11/1989 | Zarowitz |
| 4,896,946 A | 1/1990 | Suzuki et al. |
| 4,930,263 A | 6/1990 | Rando |
| 4,950,246 A | 8/1990 | Muller |
| 4,959,056 A | 9/1990 | Dombrowski et al. |
| 4,978,335 A | 12/1990 | Arthur |
| 5,053,715 A | 10/1991 | Andermo |
| 5,059,776 A | 10/1991 | Antes |
| 5,077,635 A | 12/1991 | Bollhagen |
| 5,078,683 A | 1/1992 | Sancoff et al. |
| 5,091,798 A | 2/1992 | Hibino |
| 5,132,026 A | 7/1992 | Baluyet et al. |
| 5,153,827 A | 10/1992 | Courte et al. |
| 5,159,181 A | 10/1992 | Bartels et al. |
| 5,174,766 A | 12/1992 | Yoshizawa et al. |
| 5,176,502 A | 1/1993 | Sanderson |
| 5,196,683 A | 3/1993 | Marom et al. |
| 5,271,527 A | 12/1993 | Haber et al. |
| 5,305,147 A | 4/1994 | Hasegawa et al. |
| 5,311,364 A | 5/1994 | Kanoshima et al. |
| 5,317,506 A | 5/1994 | Coutre et al. |
| 5,336,871 A | 8/1994 | Colgate, Jr. |
| 5,379,131 A | 1/1995 | Yamazaki |
| 5,394,206 A | 2/1995 | Cocca |
| 5,403,616 A | 4/1995 | Hattori et al. |
| 5,418,649 A | 5/1995 | Igarashi |
| 5,422,472 A | 6/1995 | Tavislan et al. |
| 5,430,278 A | 7/1995 | Krieg et al. |
| 5,432,329 A | 7/1995 | O'Boyle et al. |
| 5,461,239 A | 10/1995 | Atherton |
| 5,523,560 A | 6/1996 | Manique et al. |
| 5,569,212 A | 10/1996 | Brown |
| 5,585,615 A | 12/1996 | Iwanami et al. |
| 5,593,390 A | 1/1997 | Castellano et al. |
| 5,628,309 A | 5/1997 | Brown |
| 5,637,854 A | 6/1997 | Thomas |
| 5,643,212 A | 7/1997 | Coutre et al. |
| 5,675,380 A | 10/1997 | Florent et al. |
| 5,686,725 A | 11/1997 | Maruyama et al. |
| 5,747,350 A | 5/1998 | Sattler |
| 5,757,521 A | 5/1998 | Walters et al. |
| 5,764,457 A | 6/1998 | Uhde et al. |
| 5,777,303 A | 7/1998 | Berney |
| 5,782,814 A | 7/1998 | Brown et al. |
| 5,786,584 A | 7/1998 | Button et al. |
| 5,791,880 A | 8/1998 | Wilson |
| 5,792,117 A | 8/1998 | Brown |
| 5,793,502 A | 8/1998 | Bianco |
| 5,821,521 A | 10/1998 | Bridgelall et al. |
| 5,821,524 A | 10/1998 | Horlbeck |
| 5,876,380 A | 3/1999 | Manganini et al. |
| 5,880,683 A | 3/1999 | Brandestini |
| 5,882,463 A | 3/1999 | Tompkin et al. |
| 5,895,369 A | 4/1999 | Flower |
| 5,902,990 A | 5/1999 | Stewart |
| 5,920,198 A | 7/1999 | Suzuki et al. |
| 5,925,867 A | 7/1999 | Hagimoto |
| 5,954,700 A | 9/1999 | Kovelman |
| 5,986,585 A | 11/1999 | Pusch |
| 6,003,775 A | 12/1999 | Ackley |
| 6,019,745 A | 2/2000 | Gray |
| 6,047,892 A | 4/2000 | Schuessler et al. |
| 6,053,415 A | 4/2000 | Norwood |
| 6,068,615 A | 5/2000 | Brown et al. |
| 6,090,064 A | 7/2000 | Reilly et al. |
| 6,110,148 A | 8/2000 | Brown et al. |
| 6,110,152 A | 8/2000 | Kovelman |
| 6,168,080 B1 | 1/2001 | Verschuur et al. |
| 6,177,683 B1 | 1/2001 | Kolesar et al. |
| 6,202,929 B1 | 3/2001 | Verschuur et al. |
| 6,215,508 B1 | 4/2001 | Bryan et al. |
| 6,230,927 B1 | 5/2001 | Schoonen et al. |
| 6,265,466 B1 | 7/2001 | Glatkowski et al. |
| 6,274,092 B1 | 8/2001 | Itoh |
| 6,329,813 B1 | 12/2001 | Andermo |
| 6,352,523 B1 | 3/2002 | Brown et al. |
| 6,372,293 B1 | 4/2002 | Mathus et al. |
| 6,435,175 B1 | 8/2002 | Stenzler |
| 6,475,192 B1 | 11/2002 | Reilly et al. |
| 6,533,183 B2 | 3/2003 | Aasmul et al. |
| 6,598,796 B2 | 7/2003 | Harrop |
| 6,652,812 B1 | 11/2003 | Vartiainen et al. |
| 6,669,090 B2 | 12/2003 | Eilersen |
| 6,700,391 B2 | 3/2004 | Strack et al. |
| 6,743,202 B2 | 6/2004 | Hirschman et al. |
| 6,813,868 B2 | 11/2004 | Baldwin et al. |
| 6,854,653 B2 | 2/2005 | Eilersen |
| 6,876,209 B2 | 4/2005 | Lin et al. |
| 6,954,700 B2 | 10/2005 | Higashida et al. |
| 6,957,522 B2 | 10/2005 | Baldwin et al. |
| 6,976,349 B2 | 12/2005 | Baldwin et al. |
| 6,994,261 B2 | 2/2006 | Eilersen |
| 7,018,363 B2 | 3/2006 | Cowan et al. |
| 7,041,941 B2 | 5/2006 | Faries et al. |
| 7,061,831 B2 | 6/2006 | De La Huerga |
| 7,077,332 B2 | 7/2006 | Verschuur et al. |
| 7,104,973 B2 | 9/2006 | Woolston et al. |
| 7,108,184 B2 | 9/2006 | Mase et al. |
| 7,138,806 B2 | 11/2006 | Gafner et al. |
| 2001/0001472 A1 | 5/2001 | Sano et al. |
| 2001/0013544 A1 | 8/2001 | Rathus et al. |
| 2001/0015202 A1 | 8/2001 | Miller |
| 2001/0034506 A1 | 10/2001 | Hirschman et al. |
| 2002/0000471 A1 | 1/2002 | Aasmul et al. |
| 2002/0012176 A1 | 1/2002 | Ning |
| 2002/0020654 A1 | 2/2002 | Eilersen |
| 2002/0022821 A1 | 2/2002 | Eilersen |
| 2002/0063156 A1 | 5/2002 | Marchand |
| 2002/0106309 A1 | 8/2002 | Mathus et al. |
| 2002/0117549 A1 | 8/2002 | Lee |
| 2002/0117579 A1 | 8/2002 | Kotoulas et al. |
| 2002/0123078 A1 | 9/2002 | Seul et al. |
| 2003/0015590 A1 | 1/2003 | Chen |
| 2003/0039590 A1 | 2/2003 | Lodge |
| 2003/0116630 A1 | 6/2003 | Carey et al. |
| 2003/0143614 A1 | 7/2003 | Drmanac |
| 2003/0205625 A1 | 11/2003 | Eilersen |
| 2003/0233069 A1 | 12/2003 | Gillespie et al. |
| 2004/0008853 A1 | 1/2004 | Pelrine et al. |
| 2004/0024368 A1 | 2/2004 | Broselow |
| 2004/0046032 A1 | 3/2004 | Urano et al. |
| 2004/0051368 A1 | 3/2004 | Caputo et al. |
| 2004/0141426 A1 | 7/2004 | Kawasaki et al. |
| 2004/0155113 A1 | 8/2004 | Urano et al. |
| 2004/0178255 A1 | 9/2004 | Eich et al. |
| 2004/0200558 A1 | 10/2004 | Stevens et al. |
| 2004/0207385 A1 | 10/2004 | Gafner et al. |
| 2004/0210199 A1 | 10/2004 | Atterbury et al. |
| 2005/0006472 A1 | 1/2005 | Verschuur et al. |
| 2005/0035207 A1 | 2/2005 | Philyaw et al. |
| 2005/0060059 A1 | 3/2005 | Klein et al. |
| 2005/0116033 A1 | 6/2005 | Moore |
| 2005/0156318 A1 | 7/2005 | Douglas |
| 2005/0182360 A1 | 8/2005 | Yeandel et al. |
| 2005/0236603 A1 | 10/2005 | Faris |
| 2005/0283116 A1 | 12/2005 | Eakins et al. |
| 2006/0097877 A1 | 5/2006 | Baba et al. |
| 2006/0118612 A1 | 6/2006 | Christoffersen et al. |
| 2006/0125491 A1 | 6/2006 | Grishin et al. |

(56) References Cited

U.S. PATENT DOCUMENTS

| | | |
|---|---|---|
| 2006/0129104 A1 | 6/2006 | Cowan et al. |
| 2006/0138233 A1 | 6/2006 | Kemppainen et al. |
| 2006/0164002 A1 | 7/2006 | O'Brien et al. |
| 2006/0170981 A1 | 8/2006 | Ricks et al. |
| 2006/0175427 A1 | 8/2006 | Jonientz et al. |
| 2006/0176267 A1 | 8/2006 | Honeyman et al. |
| 2006/0224123 A1 | 10/2006 | Friedli et al. |
| 2006/0226238 A1 | 10/2006 | Salib et al. |
| 2006/0243804 A1 | 11/2006 | Christoffersen et al. |
| 2007/0080234 A1 | 4/2007 | Demoy |
| 2007/0239116 A1 | 10/2007 | Follman et al. |
| 2008/0015510 A1 | 1/2008 | Sandoz et al. |
| 2009/0088701 A1 | 4/2009 | Larsen |

FOREIGN PATENT DOCUMENTS

| | | |
|---|---|---|
| DE | 2636634 | 2/1978 |
| DE | 3236374 A1 | 4/1984 |
| DE | 3712089 | 10/1988 |
| DE | 4234016 | 10/1991 |
| DE | 4402319 | 8/1994 |
| DE | 19504111 | 8/1995 |
| DE | 19637967 | 9/1996 |
| DE | 19814687 | 2/1999 |
| DE | 10035192 | 10/2001 |
| EP | 0235691 | 2/1987 |
| EP | 248165 | 12/1987 |
| EP | 398717 | 11/1990 |
| EP | 402553 | 12/1990 |
| EP | 422482 A2 | 4/1991 |
| EP | 0364010 | 4/1993 |
| EP | 626660 | 11/1994 |
| EP | 685810 | 12/1994 |
| EP | 0690457 | 5/1995 |
| EP | 0336778 | 12/1995 |
| EP | 716290 | 6/1996 |
| EP | 0492954 | 10/1996 |
| EP | 833273 | 4/1998 |
| EP | 0833278 | 4/1998 |
| EP | 0573129 | 8/1998 |
| EP | 0911859 | 10/1998 |
| EP | 0588427 | 11/1998 |
| EP | 1142643 | 10/2001 |
| EP | 1143643 | 10/2001 |
| EP | 1246127 | 3/2002 |
| EP | 1193641 | 4/2002 |
| EP | 1462134 A1 | 9/2004 |
| EP | 1503185 | 2/2005 |
| FR | 2771111 | 5/1999 |
| GB | 2088163 | 6/1982 |
| GB | 2159007 | 11/1985 |
| GB | 2216259 | 10/1989 |
| GB | 2287551 | 9/1995 |
| GB | 2309801 | 8/1997 |
| GB | 2336927 | 11/1999 |
| GB | 2341965 | 3/2000 |
| JP | 56-094475 A | 7/1981 |
| JP | 59-131917 A | 7/1984 |
| JP | 63-100303 A | 5/1988 |
| JP | 2-85370 A | 3/1990 |
| JP | 2-188702 | 7/1990 |
| JP | 2-250083 | 10/1990 |
| JP | 3-27037 A | 2/1991 |
| JP | 4-222084 A | 8/1992 |
| JP | 4-233680 A | 8/1992 |
| JP | 4-233684 A | 8/1992 |
| JP | 5006449 A | 1/1993 |
| JP | 5-500917 | 2/1993 |
| JP | 05-314296 | 11/1993 |
| JP | 6-163027 | 6/1994 |
| JP | 06-171194 A | 6/1994 |
| JP | 6-333102 | 12/1994 |
| JP | 7-098752 | 4/1995 |
| JP | 07-271890 | 10/1995 |
| JP | 8-106648 | 4/1996 |
| JP | 8-118864 | 5/1996 |
| JP | 8-179475 | 7/1996 |
| JP | 8-220994 | 8/1996 |
| JP | 8-262980 | 10/1996 |
| JP | 9-16703 | 1/1997 |
| JP | 09-034361 | 2/1997 |
| JP | 9-91364 | 4/1997 |
| JP | 9-192220 | 7/1997 |
| JP | 09-223181 | 8/1997 |
| JP | 09-274637 | 10/1997 |
| JP | 10-105635 | 4/1998 |
| JP | 10-268777 | 10/1998 |
| JP | 11-135172 | 5/1999 |
| JP | 11-162591 | 6/1999 |
| JP | 11-180079 | 7/1999 |
| JP | 11-276583 A | 10/1999 |
| JP | 11-316877 | 11/1999 |
| JP | 2000-040119 | 2/2000 |
| JP | 2000-272191 | 3/2000 |
| JP | 2001-043301 | 2/2001 |
| JP | 2001-075480 | 3/2001 |
| JP | 2002-082120 | 3/2002 |
| JP | 2002-517737 | 6/2002 |
| JP | 4-233624 B2 | 12/2008 |
| WO | WO 91/04759 | 4/1991 |
| WO | WO 92/17231 | 10/1992 |
| WO | WO 93/12828 | 7/1993 |
| WO | WO 94/08647 | 4/1994 |
| WO | WO 94/12235 | 6/1994 |
| WO | 94/15120 A1 | 7/1994 |
| WO | WO 95/24317 | 9/1995 |
| WO | WO 95/28190 | 10/1995 |
| WO | 98/02130 A1 | 1/1998 |
| WO | WO 99/60533 | 11/1999 |
| WO | WO 99/65548 | 12/1999 |
| WO | WO 00/42678 | 1/2000 |
| WO | WO 01/22348 | 3/2001 |
| WO | WO 01/54055 | 7/2001 |
| WO | WO 01/62322 | 8/2001 |
| WO | WO 01/70304 | 9/2001 |
| WO | WO 01/84542 | 11/2001 |
| WO | 0195959 A1 | 12/2001 |
| WO | WO 02/11792 | 2/2002 |
| WO | WO 02/13133 | 2/2002 |
| WO | WO 02/092153 | 11/2002 |
| WO | WO 02/095675 | 11/2002 |
| WO | WO 03/017915 | 3/2003 |
| WO | WO 03-020598 | 3/2003 |
| WO | WO 03/038738 | 5/2003 |
| WO | WO 2004/084795 | 10/2004 |
| WO | WO 2004/097715 | 11/2004 |
| WO | WO 2005/075010 | 8/2005 |
| WO | WO 2005/089835 | 9/2005 |
| WO | 2005/110387 A2 | 11/2005 |
| WO | 2006/113521 A2 | 10/2006 |
| WO | 2006/120182 A1 | 11/2006 |
| WO | WO 2007/039148 | 4/2007 |
| WO | WO 2007/107562 | 9/2007 |
| WO | WO 2007/116090 | 10/2007 |
| WO | WO 2007/122253 | 11/2007 |
| WO | WO 2009/015933 | 2/2009 |

OTHER PUBLICATIONS

English Abstract for DE4234016.
English Abstract for DE19637967.
International Search Report for PCT/EP07/054069, mailed Sep. 17, 2007.
International Search Report for PCT/EP07/053558, mailed Jul. 23, 2007.
International Search Report for PCT/EP06/009240, mailed Jan. 4, 2007.
CN 1051152 English Abstract, Sep. 15, 1993.
CN 1013704 English Abstract, Aug. 28, 1991.
DE 19814687 Machine Translation, Feb. 18, 1999.
DE 19504111 Machine Translation, Aug. 10, 1995 DE 19504111.
DE 10035192 Machine Translation, Oct. 11, 2001, DE 10035192.

(56) References Cited

OTHER PUBLICATIONS

DE 2636634 English Abstract, Feb. 16, 1978.
FR 2771111 Machine Translation, May 21, 1999.
JP 2002-517737 Machine Translation, Jun. 18, 2002.
JP 2000-040119 Machine Translation, Feb. 8, 2000.
JP 11-180079 Machine Translation, Jul. 6, 1999.
JP 11-162591 Machine Translation, Jun. 18, 1999.
JP 11-135172 Machine Translation, May 21, 1999.
JP 10-268777 Machine Translation, Oct. 9, 1998.
JP 10-105635 Machine Translation, Apr. 24, 1998.
JP 9-192220 Machine Translation, Jul. 29, 1997.
JP 9-091364 Machine Translation, Apr. 4, 1997, JP 9-091364.
JP 9-16703 Machine Translation, Jan. 17, 1997.
JP 8-262980 Machine Translation, Oct. 11, 1996.
JP 8-220994 Machine Translation, Aug. 30, 1996.
JP 8-179475 Machine Translation, Jul. 12, 1996.
JP 8-118864 Machine Translation, May 14, 1996.
JP 8-106648 Machine Translation, Apr. 23, 1996.
JP 7-098752 Machine Translation, Apr. 11, 1995.
JP 6-333102 Machine Translation, Dec. 2, 1994.
JP 63-100303A English Abstract, May 2, 1988.
JP 6-163027 Machine Translation, Jun. 10, 1994.
JP 59-131917 English Abstract, Jul. 28, 1984.
JP 5-500917 English Abstract, Feb. 25, 1993.
JP 4-233684A English Abstract, Aug. 21, 1992.
JP 4-233680A English Abstract, Aug. 21, 1992.
JP 4-233624B2 Machine Translation, Dec. 19, 2008.
JP 4-222084 English Abstract, Aug. 12, 1992.
JP 3-27037A English Abstract, Feb. 5, 1991.
JP 2-250083 English Abstract, Oct. 5, 1990.
JP 2-188702 English Abstract, Jul. 24, 1990.
JP 2-85370 English Abstract, Mar. 26, 1990.
Notice of Allowance mailed Sep. 17, 2009 in U.S. Appl. No. 11/296,991, filed Dec. 8, 2005 by Eilersen et al.
Notice of Allowance mailed Apr. 30, 2009 in U.S. Appl. No. 11/296,991, filed Dec. 30, 2009 by Eilersen et al.
Non-Final Office Action mailed Oct. 14, 2008 in U.S. Appl. No. 11/296,991, filed Dec. 8, 2005 by Eilersen et al.
Corrected Notice of Allowance mailed Jun. 19, 2005 in U.S. Appl. No. 11/232,469, filed Sep. 19, 2005 by Christoffersen et al.
Notice of Allowance mailed Jun. 8, 2009 in U.S. Appl. No. 11/232,469, filed Sep. 19, 2005 by Christoffersen et al.
Non-Final Office Action mailed Dec. 17, 2008 in U.S. Appl. No. 11/232,469, filed Sep. 19, 2005 by Christoffersen et al.
Final Office Action mailed Jul. 2, 2008 in U.S. Appl. No. 11/232,469, filed Sep. 19, 2005 by Christoffersen et al.
Non-Final Office Action mailed Jan. 3, 2008 in U.S. Appl. No. 11/232,469, filed Sep. 19, 2005 by Christoffersen et al.
Non-Final Office Action mailed Jun. 19, 2007 in U.S. Appl. No. 11/232,469, filed Sep. 19, 2005 by Christoffersen et al.
Non-Final Office Action mailed Oct. 23, 2003 in U.S. Appl. No. 10/463,915, filed Jun. 18, 2003 by Eilersen et al.
Non-Final Office Action mailed Apr. 15, 2004 in U.S. Appl. No. 10/463,915, filed Jun. 18, 2003 by Eilersen et al.
Notice of Allowance mailed Aug. 16, 2004 in U.S. Appl. No. 10/463,915, filed Jun. 18, 2003 by Eilersen et al.
Notice of Allowance mailed Aug. 13, 2003 in U.S. Appl. No. 09/925,995, filed Aug. 9, 2001 by Eilersen et al.
Non-Final Office Action mailed Nov. 12, 2002 in U.S. Appl. No. 09/925,995, filed Aug. 9, 2001 by Eilersen et al.
Notice of Allowance mailed Aug. 11, 2005 in U.S. Appl. No. 09/925,792, filed Aug. 9, 2001 by Eilersen et al.
Non-Final Office Action mailed Apr. 4, 2005 in U.S. Appl. No. 09/925,792, filed Aug. 9, 2001 by Eilersen et al.
Notice of Allowance mailed Oct. 8, 2002 in U.S. Appl. No. 09/846,799, filed May 1, 2001 by Aasmul et al.
Non-Final Office Action mailed May 8, 2002 in U.S. Application No. 09/846,799, filed May 1, 2001 by Aasmul et al.
English Language Abstract of JP 09-034361.
English Language Abstract of DE 3712089.
English Language Abstract of JP 2001-075480.
English Language Abstract of JP 2002-082120.
English Language Abstract of JP 2001-043301.
English Language Abstract of JP 2000-272191 (provided by EPO).
English Language Abstract of JP 05-314296.
English Language Abstract of JP07-271890.
English Language Abstract of JP 09-223181.
English Language Abstract of JP 09-274637.
English Language Abstract of JP 11-316877.
English Language Abstract of WO 0122348.
Office Action dated Jan. 4, 2008 from U.S. Appl. No. 11/396,889, filed Apr. 3, 2006 by Christoffersen et al.

a)

b)

a)

b)

CONTACT FREE READING OF CARTRIDGE IDENTIFICATION CODES

CROSS-REFERENCE TO RELATED APPLICATIONS

This application is a 35 U.S.C. §371 national stage application of International Patent Application PCT/EP2007/052634 (published as WO 2007/107562), filed Mar. 20, 2007, which claimed priority of European Patent Application 06005597.7, filed Mar. 20, 2006; this application further claims priority under 35 U.S.C. §119 of U.S. Provisional Application 60/788,204, filed Mar. 31, 2006.

FIELD OF THE INVENTION

The present invention provides an alternative arrangement and method for contact free reading of identification codes on medicament containing reservoirs, such as cartridges or flexible reservoirs. In particular, the present invention relates to a medicament containing reservoir for a medication delivery device. The reservoir has an identification code arranged on an exterior surface thereof. This identification code comprises a plurality of electrode elements adapted to interact with a transmitter/receiver arrangement arranged on an associated medication delivery device.

BACKGROUND OF THE INVENTION

WO 01/84542 discloses a cartridge for a medication delivery device, the cartridge carrying an identification code represented by a number of bars. The bars are arranged perpendicular to the axis of the cartridge. Each bar is along its entire length provided with an optical grating which diffracts and reflects light impinging the surface carrying the identification code. In this way a minor part of the impinging light is reflected from the surface of the bar as a set of light beams of which beams at least one is detected for the indication of the presence of the bar when said bar passes a reading light field. The reflections from the bars may be interpreted as representing "1"s and "0"s in a binary code. Thus, in order to read the identification codes suggested in WO 01/84542 a sophisticated optical detection system is required.

U.S. Pat. No. 6,110,152 discloses a cartridge for containing a fluid and for use with an electronic delivery device. The cartridge of U.S. Pat. No. 6,110,152 includes a housing for holding the fluid and an information providing source. The information providing source is coupled to the cartridge housing to operatively couple with the electronic delivery device to provide predetermined information regarding the cartridge to the electronic delivery device. For example, the information providing source may be a set of wires and contacts, or contact bands, that provide the predetermined information to the electronic delivery device by producing a binary code. Alternatively, the information providing source is a bar code that provides the predetermined information to electronic delivery device by reading of the bar code. The cartridge may be used in a system that includes an electronic delivery device, such as an electronic pen-type injector and/or infusion pump. It should be noted that in order to read the information providing source on the cartridge an electrical connection should be provided between the information providing source and the electronic delivery device.

WO 2004/084795 relates to marking of cartridges or similar devices. The marking can be in an electronically readable form while being transparent. The transparent conductor can be in form of a polymer, an ITO and the like. Similar to U.S. Pat. No. 6,110,152 electrical connections need to be established between the transparent conductors and an associated medication delivery device in order to read the marking.

U.S. Pat. No. 4,420,754 discloses a system for measuring the relative movement between two elements, such as the scale and slide of a hand-held measuring instrument. The system according to U.S. Pat. No. 4,420,754 includes the provision of a number of groups of supply electrodes on the slide. Each of these electrodes in each group being supplied from a respective one of a multiple number of output signals from a signal generator so that all of the supply electrodes are furnished with voltages according to a cyclic pattern. The slide also has at least one receiving electrode which feeds a signal processing unit. The scale is provided with an electronic pattern comprising internally galvanically connected parts, one being a detecting part, located close to the area where the supply electrodes of the slide are moved, the other of the two parts being a transferring part which is located close to the area where the receiving electrode of the slide is moved. The movement of the slide along the scale generates a signal from the receiving electrode which is derived from the signals from at least two adjacent supply electrodes and the position of the slide is determined by a signal processing unit which identifies the amplitude ratio of the received signals. Thus, the system suggested in U.S. Pat. No. 4,420,754 relates to an arrangement for detecting relative movements between two elements.

It is an object of the present invention to provide a solution involving an identification code in form of electrode elements arranged on the cartridge, said identification code being readable by an arrangement of transmitters and receivers arranges on an associated medication delivery device.

It is an advantage of the present invention that the identification code provided on medicament containing cartridges may be easily readable by contact free means. Thus, no sophisticated detection systems such as optical detection systems are required.

SUMMARY OF THE INVENTION

The above-mentioned object is complied with by providing, in a first aspect, a cartridge adapted to contain a medicament, the cartridge further being adapted to be inserted into an associated medication delivery device, the cartridge comprising a plurality of electrode elements arranged on an exterior surface part of the cartridge, wherein an electrode element of said plurality of electrode elements comprises a receiver zone and a transmitter zone, said receiver and transmitter zones being electrically connected, said receiver zone and said transmitter zone being adapted to electrically couple to one or more transmitters and to one or more receivers, respectively, said one or more transmitters and said one or more receivers being arranged on the associated medication delivery device.

The plurality of electrode elements may be made of an electrically conducting material. Such electrically conducting material may be an optically transparent or non-transparent material. The electrode elements may be galvanically separated. Thus, only corresponding receiver and transmitter zones of the same electrode element are galvanically connected.

The plurality of transmitter zones of the plurality of electrode elements may form a first array on the exterior surface part of the cartridge. Similarly, the plurality of receiver zones of the plurality of electrode elements may form a second array on the exterior surface part of the cartridge. The first and second arrays may be laterally shifted or laterally displaced relative to each other. This laterally shifting or displacement may be a measure of the identification code of the cartridge. To reduce mechanical wear the electrode elements may be at least partly covered by a layer of dielectric material.

The cartridge may comprise a rear end and a front end, the front end comprising an arrangement for securing an injection needle to the cartridge—optionally via a cartridge holder into which the cartridge is adapted to be inserted. The plurality of electrode elements may be arranged near the rear end of the cartridge so that the plurality of electrode elements have a spatial overlap with a displaceable rubber piston when said piston is in its initial position.

The plurality of electrode elements may form an essentially periodic pattern, the direction of periodicity being substantially perpendicular to an axial direction of the cartridge. Preferably, the essentially periodic pattern forms an essentially unbroken path around the exterior surface part of the cartridge whereby the identification of cartridge becomes independent of the angular orientation of the cartridge when inserted into the medication delivery device.

As previously mentioned, the plurality of electrode elements may be made of an optically transparent material. By applying optically transparent electrode elements the electrode elements are allowed to occupy more space on the cartridge. In case of optically transparent electrode elements the cartridge may have an axial direction, wherein the plurality of electrode elements form an essentially periodic pattern, the direction of periodicity being substantially parallel to the axial direction of the cartridge The plurality of electrode elements, transparent or non-transparent, may be arranged on a flexible foil, said foil being secured to the exterior surface part of the cartridge using an adhesive between the foil and the exterior surface part.

The plurality of electrode elements may be adapted to couple to one or more transmitters and to one or more receivers arranged on the associated medication delivery device in a preferably capacitive manner. However, coupling between electrode elements and transmitters/receivers may also be accomplished by inductive means.

The cartridge may also be of a different kind. Thus, the cartridge may comprise one or more collapsible sidewall portions, said one or more collapsible sidewall portions being adapted to collapse during emptying of the cartridge.

In a second aspect, the present invention relates to a method for identifying a type of medicament in a medicament containing cartridge when said cartridge is mounted in an associated medication delivery device, the method comprising the steps of providing a medicament containing cartridge comprising a plurality of electrode elements arranged on an exterior surface part thereof, wherein a number of said plurality of electrode elements comprises a receiver and a transmitter zone being electrically connected in pairs, providing a plurality of electrical input signals to respective transmitters arranged on the associated medication delivery device, and electrically couple the plurality of electrical input signals from the respective transmitters to respective receiver zones of a group of said plurality of electrode elements, receiving a plurality of electrical output signals from a plurality of receivers arranged on the associated medication delivery device, the plurality of receivers being electrically coupled to transmitter zones of said group of electrode elements, and identifying the type of medicament in accordance with the electrical output signals received from the plurality of receivers.

The respective transmitters may be capacitively coupled to respective receiver zones of the group of said plurality of electrode elements, and wherein the plurality of receivers are capacitively coupled to transmitter zones of said group of electrode elements.

In one embodiment of the present invention four electrical input signals are applied to four transmitters arranged on the associated medication delivery. These four electrical input signals are approximately 90 degrees out of phase so as to form a quadrature electrical input signal. Each electrical input signal may oscillate with a frequency within the range 50 kHz-150 kHz, such as within the range 90 kHz-110 kHz. However, other frequency ranges may also be applicable.

In a third aspect, the present invention relates to a medication delivery device comprising a cartridge according to the first aspect of the present invention.

In a fourth aspect, the present invention relates to a flexible foil adapted to be arranged on an exterior surface part of a medicament containing cartridge, the flexible foil comprising a plurality of electrode elements, wherein an electrode element of said plurality of electrode elements comprises a receiver zone and a transmitter zone, said receiver and transmitter zones being electrically connected, said receiver zone and said transmitter zone being adapted to electrically couple to one or more transmitters and to one or more receivers, respectively. In this fourth aspect the plurality of electrode elements may be provided on a lower surface of the flexible foil whereby the foil itself may form a protective layer over the plurality of electrode elements when the foil is attached to a cartridge, In a fifth aspect, the present invention relates to a medication delivery device having a medicament containing cartridge inserted therein, the medicament containing cartridge comprising a plurality of electrode elements arranged on an exterior surface part of the cartridge, wherein an electrode element of said plurality of electrode elements comprises a receiver zone and a transmitter zone, said receiver and transmitter zones being electrically connected, the medication delivery device further comprising a reading means comprising one or more transmitters and one or more receivers, wherein said one or more transmitters being adapted to electrically couple to at least one receiver zone, and wherein said one or more receivers being adapted to electrically couple to at least one transmitter zone. Preferably, the electrical coupling between the transmitter and receiver zones and the reading means of the medication delivery device is of capacitive nature.

BRIEF DESCRIPTION OF THE DRAWINGS

The present invention will now be explained in further details with reference to the accompanying figures, wherein.

Figure 1:
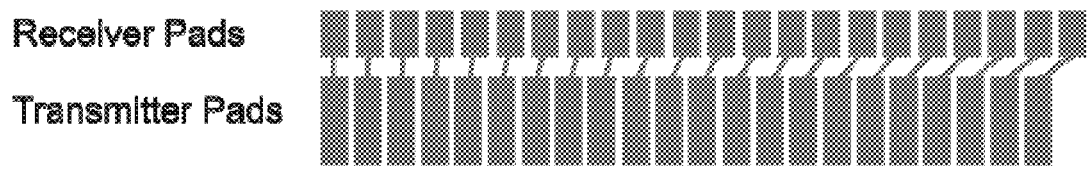
FIG. 1 shows a traditional digital caliper scale.
Figure 1:
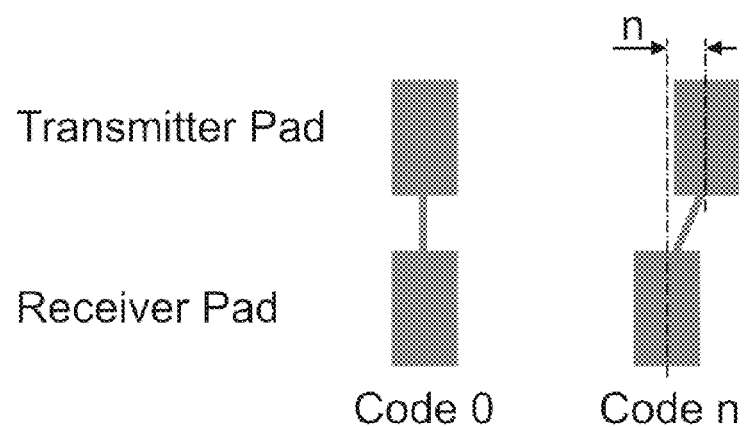

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE INVENTION

In its most general aspect the present invention relates to a medicament containing reservoir having electrode elements positioned on an exterior surface thereof. The medicament containing reservoir can be a traditional cartridge, a flexible reservoir with collapsible sidewall portions or the like. The electrode elements can be made of a transparent or non-transparent material. Suitable transparent materials are for example electrically conducting polymers or ITOs. Non-transparent electrode elements can be formed as a metallic pad or a pattern of metallic pads adapted to couple to a number of transmitters and a number of receivers arranged on an associated medication delivery device. Electrode elements of transparent or non-transparent nano-tubes can also be applied. The coupling between electrode elements and transmitters/receivers can be capacitive.

The overall principle of detection between electrode elements and a reader head comprising the transmitter/receiver arrangement is similar that disclosed in U.S. Pat. No. 4,420,754. However, in the present invention discrete values of the scale of U.S. Pat. No. 4,420,754 are associated with the various types of medicament. Thus, to a certain type of medicament a single and well-defined value is associated.

In the following the notation "cartridge" will be used only. However, it should be noted that the term cartridge should be interpreted broadly, thus covering both traditional cartridges and for example reservoirs having flexible or collapsible sidewalls. By determining a capacitive or inductive coupling between electrode elements of the cartridge and transmitter/receivers the identification code of the cartridge may be determined in a very simple and contact free manner. When the identification code of the cartridge is determined, the type of medicament contained in the cartridge is determined in an unambiguous manner. However, not only the type of medicament in the cartridge can be determined by the contact free coupling between electrode elements and the transmitter/receiver arrangement. Also data relating to fabrication date, batch number, number of available doses etc. can be determined.

Referring now to FIGS. 1a and 1b the means for deriving codes for marking cartridges are based on an absolute position measuring principle commonly used in digital calipers. The display part of a digital caliper contains the reader head whereas the scale part of the caliper holds the scale. The scale consists of two rows of metallised pads where one row—the transmitter pads—have pads equidistantly placed, and the row above—the receiver row—have pads that are also equidistantly placed but at a somewhat greater distance from each other. In this way a continuous scale is produced where the displacement of a receiver pad in relation to its connected transmitter pad in any given position along the scale is a direct measure of its absolute position on the scale. By using discrete parts of a code like the one used in some digital calipers, see FIG. 1b, a code, readable by non-contacting means, is created.

Figure 2:
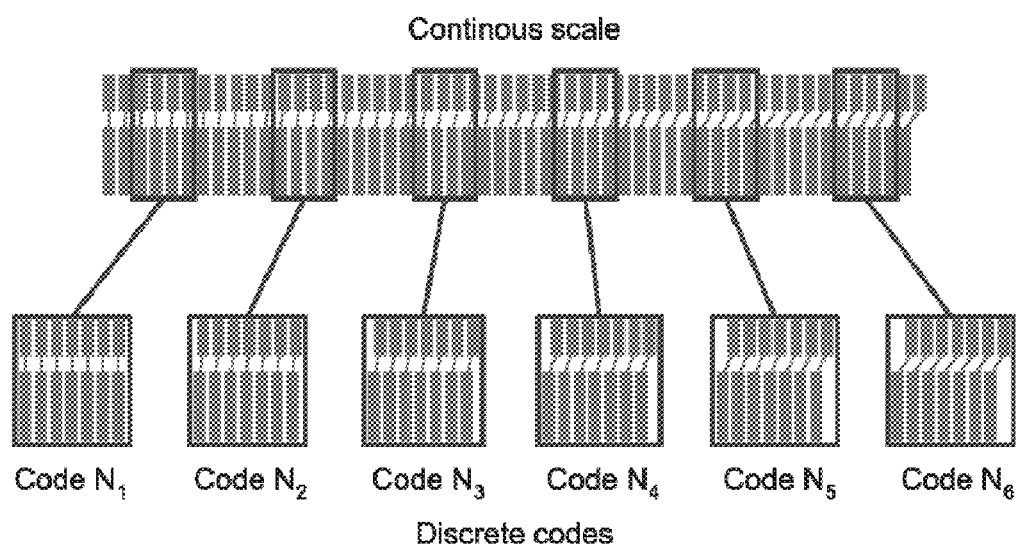
FIG. 2 shows discrete portions of a caliper scale.

As depicted in FIG. 2, the coding method according to the present invention is based on taking snippets of a continuous scale and using these as discrete codes representing the various cartridges and the drugs contained within. By spacing these snippets carefully the signal-to-noise ratio, or rather the probability of the right code read, is increased. On the other hand, the greater the safety margin between adjacent codes, the fewer the available codes.

Figure 3:
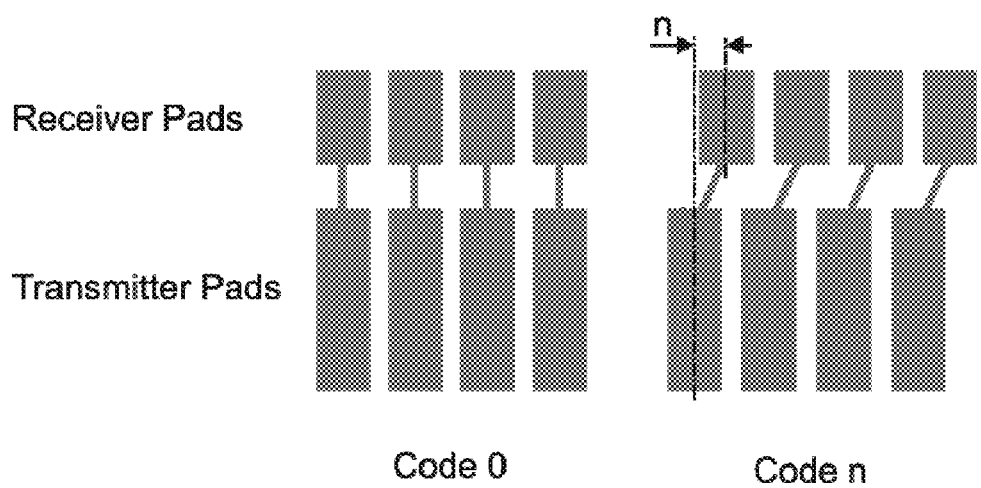
FIG. 3 illustrates a code phase shift.

The displacement of the receiver pads to their transmitter counterparts, denoted "n" in FIG. 3, is measured by a reader head that capacitively couples four sinusoidal signals in quadrature to four receiver pads on the code. The signals received are passed on to the connected transmitter pads on the code and in turn transmitted back to the receiver part of the reader head. The amplitude ratios of the received quadrature signals give a resulting sinusoidal composite signal whose phase relative to the transmitted signals from the reader head is a direct measure of the code value, and thereby the type of the medicament in the cartridge.

Figure 4:
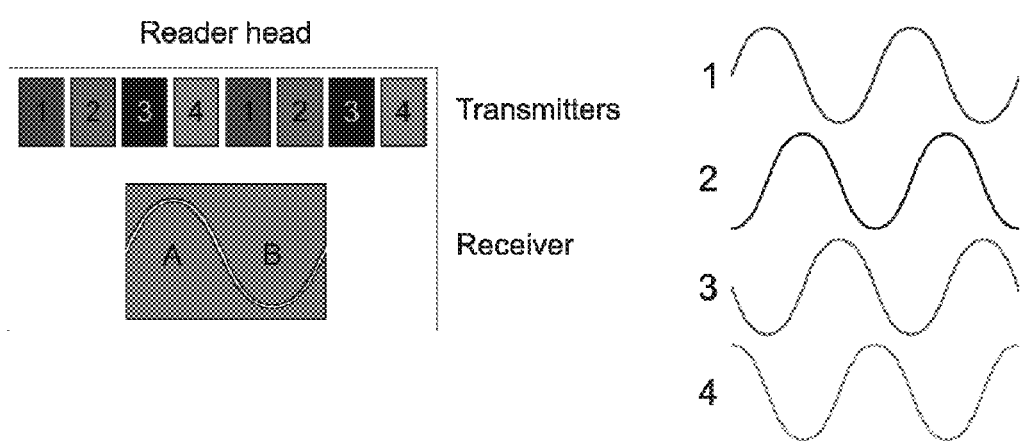
FIG. 4 shows a reader head and driver signals.
Figure 5:
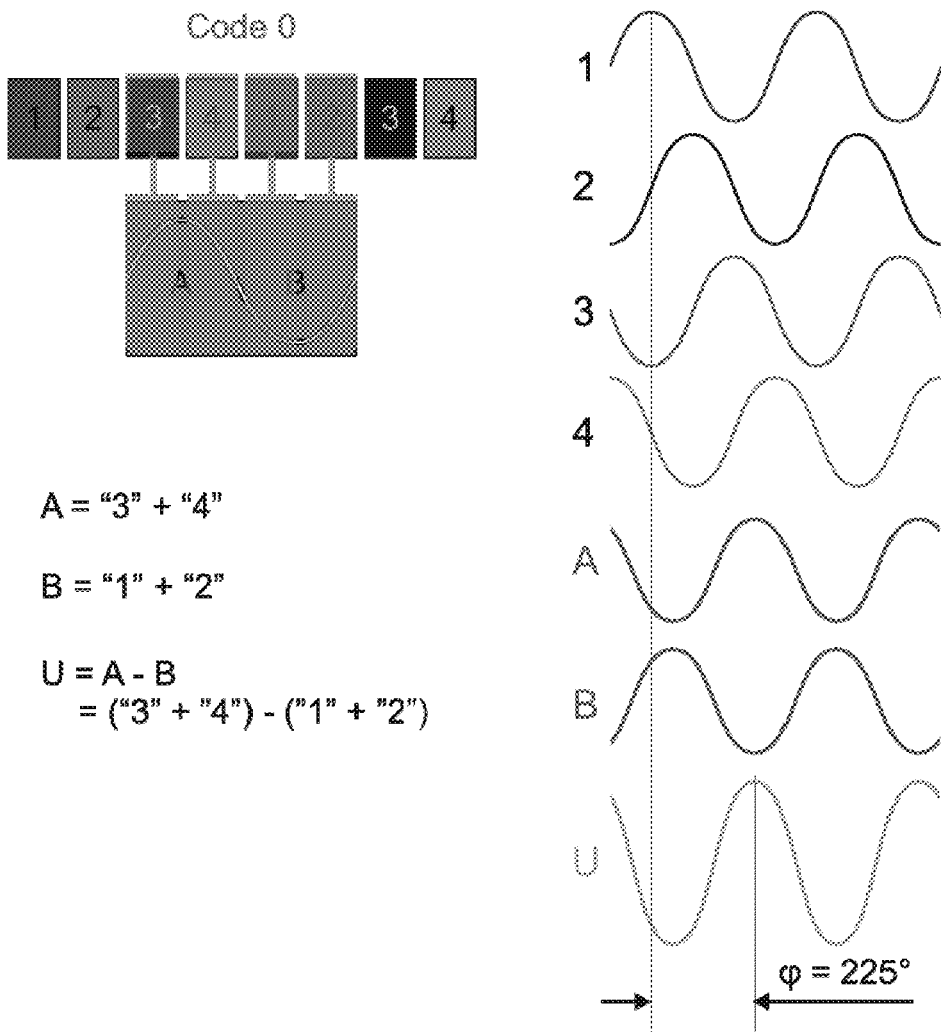
FIG. 5 illustrates driver signals and detected signal for code "0"
Figure 6:
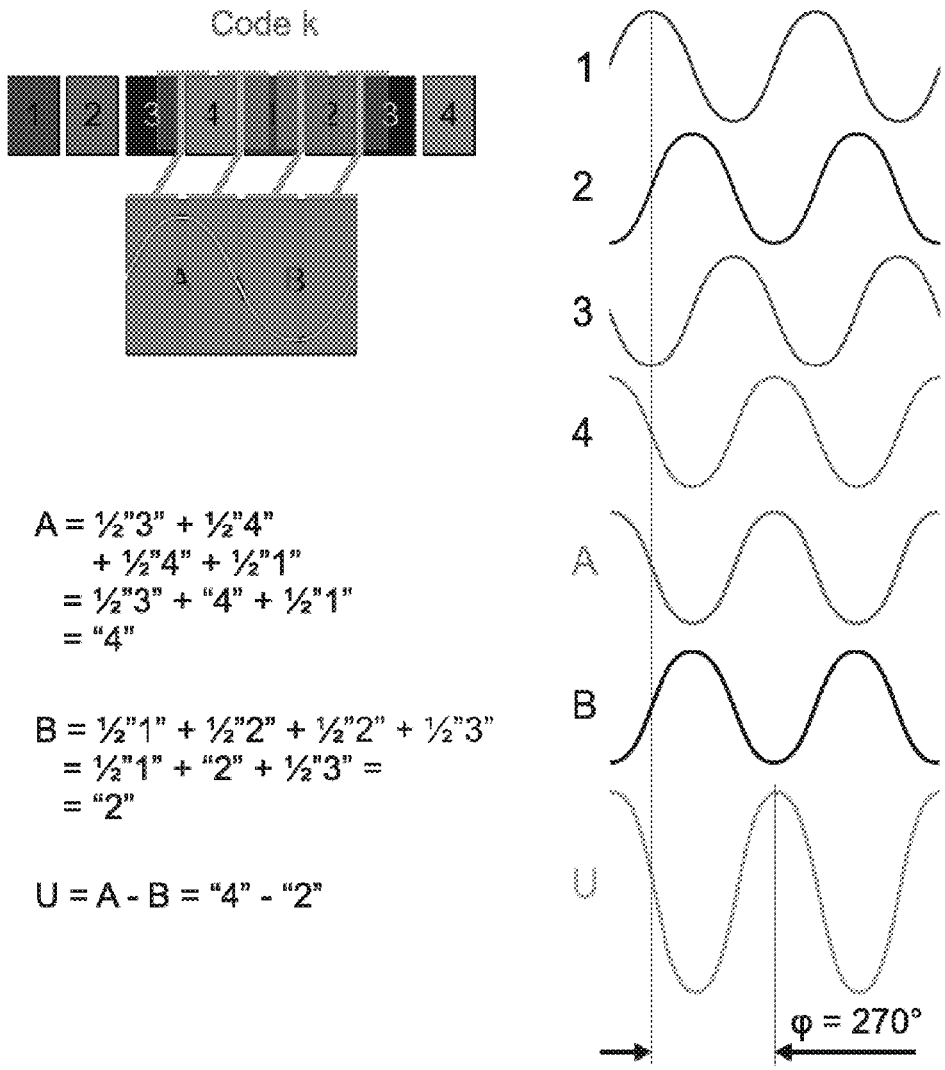
FIG. 6 illustrates driver signals and detected signal for code "n"

Some simplified examples to explain the quadrature signal summation and phase shift measurements which form the basis of the digital caliper principle are depicted in FIGS. 4-6. The reader head is pictured in FIG. 4, as are the four sinusoidal quadrature signals driving the transmitters. Note the 90° phase shift between the transmitted signals—which is the definition of quadrature. This modulation scheme—in conjunction with synchronous demodulation and phase angle measurement by waveform zero crossing time differences in the reader head ASIC—makes for a very stable output value despite the very small capacitances involved. The sinusoidally shaped receiver pads of the reader head weight the received signals in order to minimise reading disturbances when moving from one code pad to the next. This is similar to when a digital caliper is adjusted.

When the reader head is applied to a code with code value 0, which means that 'n' is zero in FIG. 3, the resulting waveforms are as illustrated in FIG. 5. As seen the signals from receivers A and B are 180 degrees out of phase. Compared to transmitter signal "1" a phase shift, $\phi$, of 225 degrees is detected. Thus, Code 0 yields a phase shift value of 225° compared to transmitter signal "1" and that the output signal U from the reader head electronics is derived from the difference between signals A and B. In this way any external noise signals that may have entered the reader head are cancelled while the output signal is doubled in amplitude. Horizontally offsetting or shifting the code relative to the reader head will, of course, still yield the same phase value from the reader head.

In another example, see FIG. 6, the reader head is applied to a code with code value k. In this case the transmitter pads of the reader head are not aligned with the receiver pads of the code. Instead two adjacent transmitter pads transmit to one receiver pad on the code. The waveforms are also illustrated in FIG. 6. Note that in the equations of these examples small terms that will cancel out in the signal processing have been eliminated. Also, the signal weighting of the reader pad shape is simplified to the weights 0, ½ or 1. A comprehensive explanation of the working principle can be found in for example U.S. Pat. No. 4,420,754.

Thus, the coding method according to the present invention involves placing an array of electrically conducting receiver pads on the medical container, such as cartridge. Each of these receiver pads are connected to a transmitter pad in an array of transmitter pads. The lateral displacement of the transmitter pad array to its receiver counterpart is the coded value. This value is measured by a reader head that by non-contacting, capacitive means transmits signals to the receiver pads on the medical container and receives, also by non-contacting, capacitive means, signal that is changed in proportion to the lateral displacement of the pad arrays on the medical container. This signal change is decoded by the electronics associated with the reader head and output as a digital code value.

In FIGS. 4-6 the number of transmitters is eight. It should be noted that the number of transmitters can be different from eight (both higher and lower). Also, other types of drive signals (other than quadrature drive signals) can be applied to the transmitters. For example, six drive signals shifted 60 degrees can be applied to six transmitters. The receiver can also be implemented differently than depicted in FIGS. 4-6. For example, the receiver can be implemented with additional periods than the one shown in FIGS. 4-6. Also, the shape of the receiver can be different from sinusoidal—for example quadratic, rectangular and triangular are also applicable shapes. The only requirement is that the receiver requires at least two receiver pads arranged 180 degrees out of phase.

Figure 7:
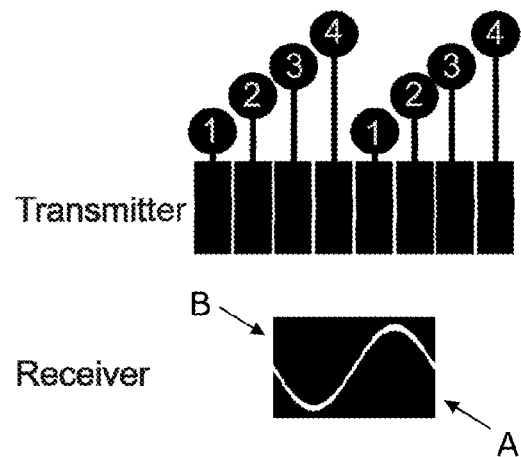
FIG. 7 shows driver head and receiver/transmitter elements.
Figure 7:
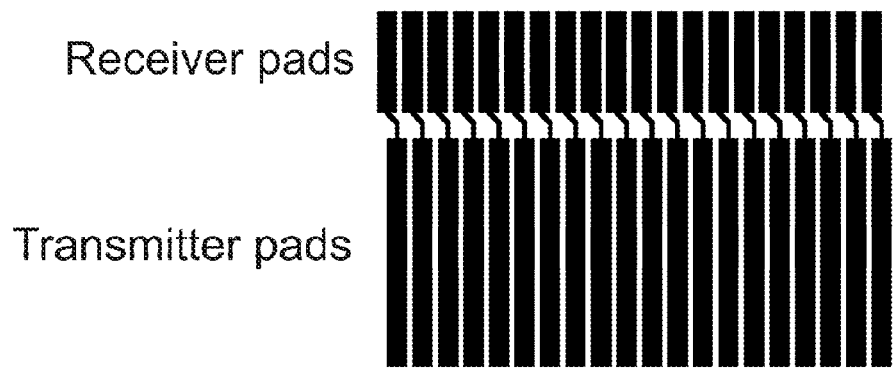

FIG. 7a shows a reader head whereas FIG. 7b shows arrays of receiver pads and transmitter pads. As depicted in FIG. 7b a constant lateral displacement exists between the receiver pads and the transmitters pads. Now referring to FIG. 7a the reader head comprises a total of eight transmitters, where transmitters "1" are driven in parallel. Similarly, transmitters "2", "3" and "4" are driven in parallel. The receiver of the reader head comprises two receiver pads "A" and "B".

Figure 8:
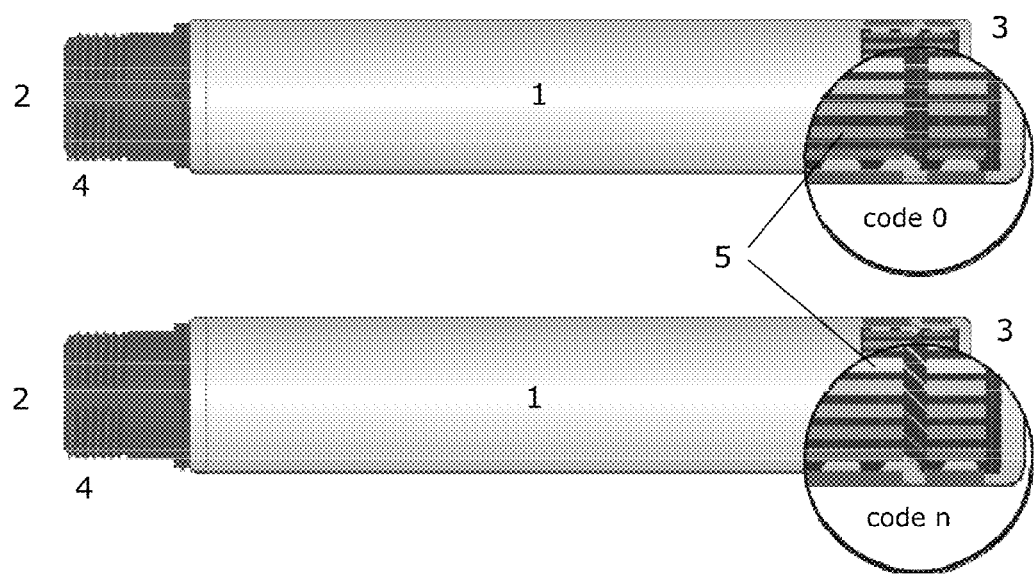
FIG. 8 shows code "0" and code "n" arranged on cartridge.

Referring now to FIG. 8 a cartridge 1 according to the present invention is depicted. As seen the cartridge comprises a body having a front end 2 and a back end 3. At the front end an arrangement for securing an injection needle (not shown) is provided. The arrangement comprises a protrusion having a threaded outer surface 4 being adapted to engage with a threaded inner surface of a mount or hub (not shown) which holds the injection needle. In order for a medicament, such as insulin, to be expelled from the cartridge a pierceable membrane is provided in or near the protrusion. This pierceable member is penetrated by an inwardly oriented needle part when the mount or hub is secured to the protrusion.

Medicament contained in the cartridge is expelled by displacing a piston (not shown) in the direction towards the front end of the cartridge. When the piston is moved in the direction of the front end the cartridge volume between the piston and the front end is decreased whereby medicament is forced to leave the cartridge via an injection needle attached to the front end of the cartridge.

On an exterior surface part of the cartridge a plurality of the electrode elements 5 are arranged. The upper cartridge in FIG. 8 carries electrode elements with code "0" whereas the lower cartridge of FIG. 8 carries electrode elements with code "n". The electrode elements may be arranged in various ways, such as for example as an essentially periodic pattern around the exterior surface of the housing. The pattern does not necessarily need to go all the way around the housing. Thus, only part of the 360 degrees around the body of the cartridge may be covered. However, according to a preferred embodiment of the present invention the pattern of electrode elements goes all around the body of the cartridge whereby the reading of the pattern becomes independent of the angular orientation of the cartridge when inserted into the associated medication delivery device.

The electrode elements depicted in FIG. 8 can be mounted or printed directly into the cartridge as electrically conducting electrodes or pads. Alternatively, the electrode elements can be printed, or by other means provided, directed on a substantially plane, flexible label. This label may have an adhesive material provided on one of its surfaces whereby the label, with the electrode elements arranged or provided thereon, can be positioned on the cartridge. The dimensions of the label are preferably matched to the dimensions of the cartridge. Thus, when the label carrying the electrode elements is arranged on the cartridge by adhesive means, the electrode elements are distributed equally around the complete circumference of the cartridge.

When the cartridge has been inserted into the medication delivery device a number of electrode elements are aligned with a reader head comprising the transmitter/receiver arrangement provided inside the medication delivery device. By aligned is meant that a number of the receiver pads are brought within capacitive coupling distance from the transmitters of the reader head. Similarly, the transmitter pads are brought within capacitive coupling distance from the receivers of the reader head. Thus, when the cartridge has been inserted in the medication delivery device the capacitance the code and thereby the ID of the cartridge can be determined. When the ID of the cartridge has been determined the type of medicament contained within the cartridge is known. In fact a control unit of the medication delivery device may be configured to accept only certain types of medicament. Thus, if the content of the cartridge does not belong to this group of medicaments a warning signal can be provided to the user of the medication delivery device informing the user that a medicament of a wrong type has been inserted into the medication delivery device. The control unit can also be configured to constantly, i.e. as long as the cartridge is positioned in the medication delivery device, reading the ID of the cartridge.

Figure 9:
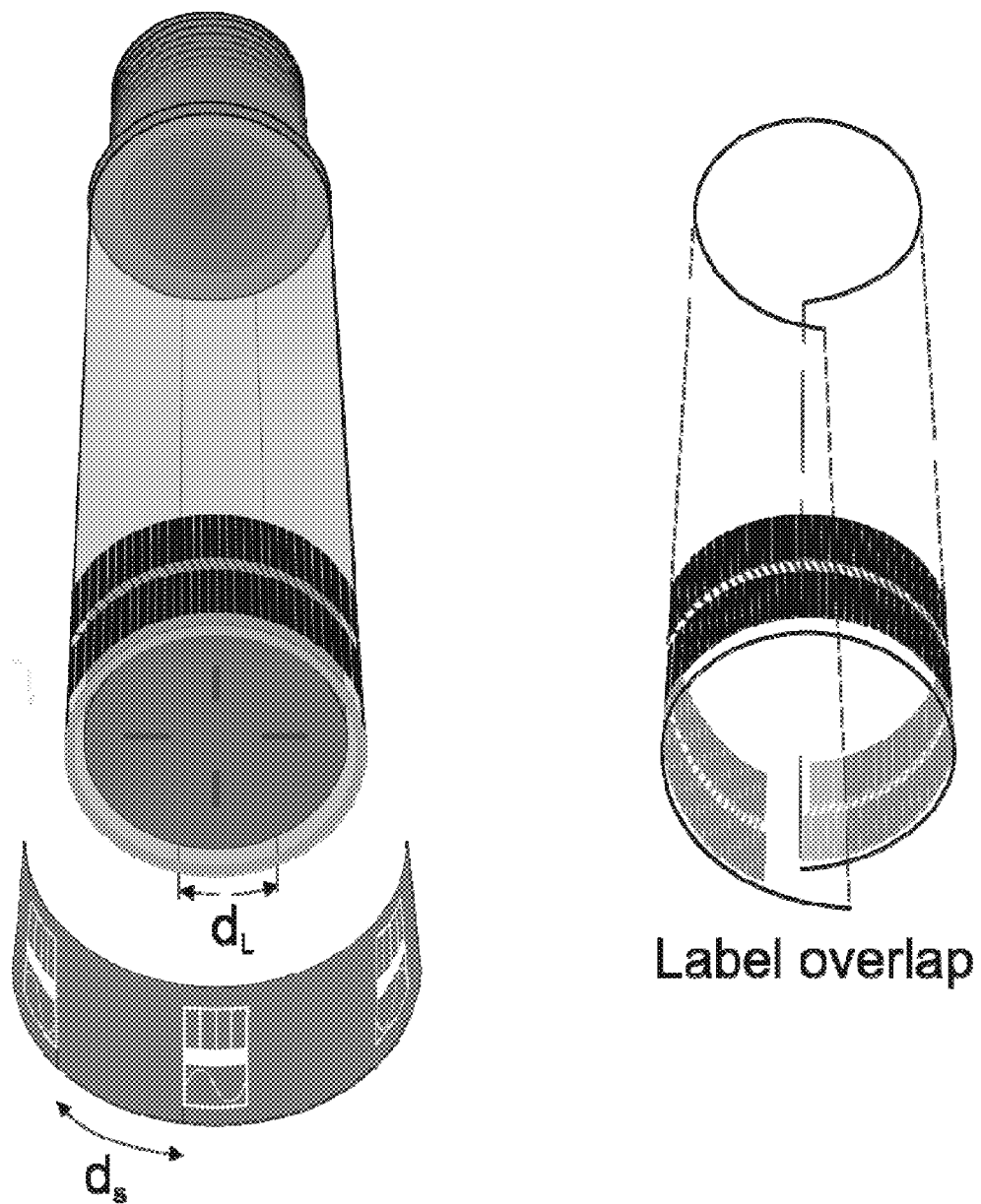
FIG. 9 shows multiple reader heads.

When reading an electronic code printed along an overlapping edge of the label attached to a cylindrically shaped cartridge, a misread of the electronic code may occur if the reader head happens to coincide with the label overlap zone when the cartridge is inserted into the medication delivery device. More than one reader head needs to be used to discriminate against and correct for such code misreads. By placing several (more than one, preferably three) reader heads along the code this problem can be solved. The distance between two adjacent reader heads, $d_s$, is greater than the label overlap $d_L$, see FIG. 9. In this way only one reader head can be affected by the label overlap.

By using three reader heads a majority voting system can be used by the device electronics to first identify the reader head placed wholly or partially over the label overlap and to compare the readings from the other reader heads. If these are reading the same code the readings are deemed to be correct. If the codes are not the same the device electronics will signal a non-read status and, for example, prompt the user to remove and re-insert the cartridge. This situation may arise from label damage or liquid contamination of the cartridge.

Figure 10:
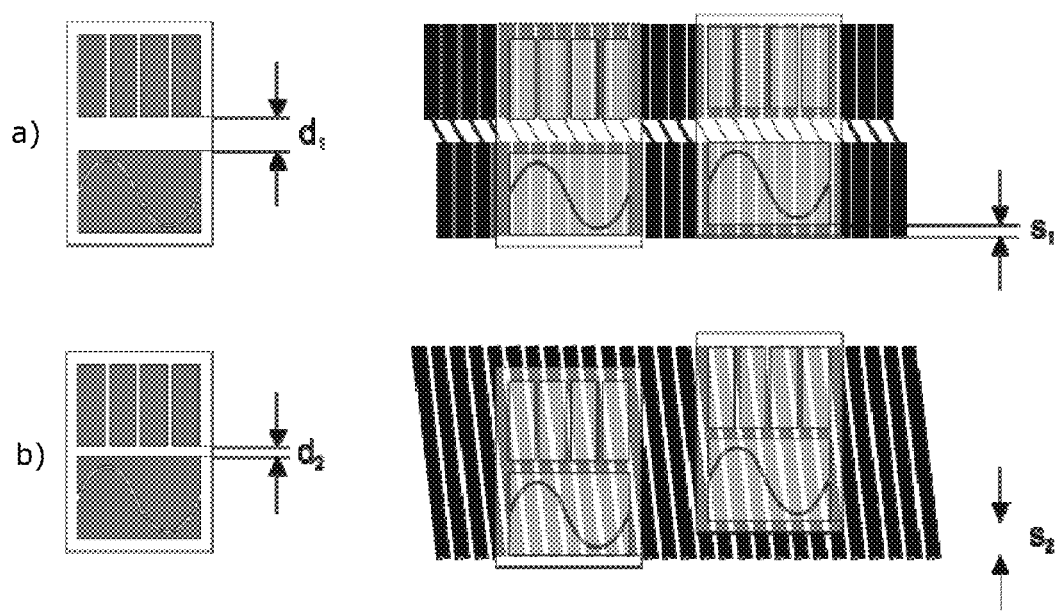
FIG. 10 shows an alternative implementation of electrode elements.

As stated above, the suggested capacitive coding scheme uses separate transmitter and receiver pads on the code itself. The pads are connected in pairs in that a transmitter pad is connected to its receiver pad by means of a thin conductor. This arrangement may limit the range of movement a reader head can have while still having full coverage of the code patterns. By substituting the transmitter-receiver pad pair with an equivalent code comprising a solid slanted bar, see FIG. 10, the reader head may be made more compact in that the transmitter and receiver parts of the reader head may be moved closer together. This more compact design of the reader head is illustrated in FIG. 10b where $d_2 < d_1$ where $d_2$ is the distance between the transmitters and the receivers in the compact design (FIG. 10b), whereas $d_1$ is the distance between the transmitters and the receivers in the non-compact design (FIG. 10a). The compact reader head can then utilise the whole range of travel perpendicular to the code, thus making the code/reader system less sensitive to misalignments in this dimension ($s_2 > s_1$).

The invention claimed is:

1. A cartridge adapted to contain a medicament, the cartridge further being adapted to be inserted into an associated medication delivery device, the cartridge having an identification code which is identifiable by the medication delivery device, the identification code comprising:
a plurality of galvanically separated electrode elements arranged on an exterior surface part of the cartridge, the plurality of electrode elements being distributed equidistantly substantially circumferentially,
wherein each of the electrode elements comprises a receiver zone which connects galvanically to a transmitter zone such that the receiver zone is adapted to receive electrical input signals, and the transmitter zone is adapted to transmit associated electrical output signals, and wherein the receiver zone of each electrode element is displaced along a first direction relatively to its respective transmitter zone, a magnitude of displacement between the transmitter zone and the receiver zone being representative of the identification code.

2. A cartridge according to claim 1, wherein the cartridge comprises a rear end and a front end, the front end comprising an arrangement for securing an injection needle to the cartridge.

3. A cartridge according to claim 2, wherein the plurality of electrode elements are arranged near the rear end of the cartridge.

4. A cartridge according to claim 2, wherein the plurality of electrode elements form an essentially periodic pattern, the direction of periodicity being substantially perpendicular to an axial direction of the cartridge.

5. A cartridge according to claim 1, wherein the plurality of electrode elements are made of an optically transparent material.

6. A cartridge according to claim 5, wherein the plurality of electrode elements form an essentially periodic pattern, the direction of periodicity being substantially parallel to an axial direction of the cartridge.

7. A cartridge according to claim 1, wherein the plurality of electrode elements are arranged on a flexible foil, said foil being secured to the exterior surface part of the cartridge using an adhesive between the foil and the exterior surface part.

8. A cartridge according to claim 1, wherein the plurality of electrode elements are at least partly covered by a layer of dielectric material.

9. A cartridge according to claim 1, wherein the cartridge has a body and wherein the electrode elements extend partly or all the way around the cartridge body.

10. A cartridge according to claim 1, wherein the medicament cartridge is a flexible reservoir which comprises one or more collapsible sidewall portions, said one or more collapsible sidewall portions being adapted to collapse during emptying of the cartridge.

11. A medication delivery device comprising:
a housing adapted to house a cartridge having an identification code, the cartridge adapted to contain a medicament,
the medicating delivery device adapted to identify the identification code of the cartridge when said cartridge is inserted therein,
a plurality of device transmitters arranged to capacitively couple to respective receiver zones of a group of electrode elements of the cartridge when inserted into a medication delivery device, the electrode elements of the cartridge distributed equidistantly substantially circumferentially on an exterior surface part of the cartridge,
a plurality of device receivers arranged to capacitively couple to respective transmitter zones of said group of electrode elements, and
wherein the medication delivery device is adapted to provide a plurality of mutually phase shifted electrical input signals to the respective device transmitters, to receive respective output signals at the plurality of device receivers, and to measure a magnitude of displacement based upon a phase change between the output signals relative to the input signals to thereby determine the identification code of the cartridge.

12. A medication delivery device according to claim 11, wherein four electrical input signals are applied to respective ones of four device transmitters.

13. A medication delivery device according to claim 12, wherein the four electrical input signals are approximately 90 degrees out of phase so as to form a quadrature electrical input signal.

14. A medication delivery device according to claim 11, wherein the electrical input signals oscillate with a frequency within the range 50 kHz-150 kHz.

15. A flexible foil adapted to be arranged on an exterior surface part of a cartridge adapted to contain a medicament, the cartridge adapted to be inserted into an associated medical delivery device, the flexible foil having an identification code which is identifiable by the medication delivery device, the identification code comprising:
a plurality of galvanically separated electrode elements, the plurality of electrode elements being distributed equidistantly substantially circumferentially along a first direction,
wherein each of the electrode elements comprises a receiver zone which connects galvanically to a transmitter zone such that the receiver zone is adapted to receive electrical input signals, and the transmitter zone is adapted to transmit associated electrical output signals,
said receiver zone and each electrode element is displaced along a first direction relatively to its respective transmitter zone, a magnitude of displacement between the transmitter zone and the receiver zone being representative of the identification code.

* * * * *